(12) United States Patent
Hayman

(10) Patent No.: US 6,503,244 B2
(45) Date of Patent: Jan. 7, 2003

(54) HIGH PRESSURE INJECTION SYSTEM

(75) Inventor: Douglas Ray Hayman, Mission Viejo, CA (US)

(73) Assignee: Micro Therapeutics, Inc., Mission Viejo, CA (US)

( * ) Notice: Subject to any disclaimer, the term of this patent is extended or adjusted under 35 U.S.C. 154(b) by 0 days.

(21) Appl. No.: 09/801,480

(22) Filed: Mar. 7, 2001

(65) Prior Publication Data

US 2002/0128631 A1 Sep. 12, 2002

(51) Int. Cl.$^7$ .............................................. A61M 25/00
(52) U.S. Cl. .................. 604/525; 604/103.09; 604/110; 604/523; 604/524; 604/243
(58) Field of Search .............................. 604/96, 97, 98, 604/100, 525, 110, 218, 263, 243, 283, 523, 524, 103.09; 285/322, 334.4, 423; 141/27, 329

(56) References Cited

U.S. PATENT DOCUMENTS

| | | | | |
|---|---|---|---|---|
| 3,752,510 A | * | 8/1973 | Windischman et al. ..... 285/322 |
| 4,187,848 A | * | 2/1980 | Taylor ........................ 604/243 |
| 4,233,975 A | * | 11/1980 | Yerman ...................... 604/110 |
| 4,547,194 A | * | 10/1985 | Moorehead ................. 604/283 |
| 5,163,903 A | | 11/1992 | Crittenden et al. |
| 5,226,898 A | * | 7/1993 | Gross ......................... 604/243 |
| 5,989,219 A | * | 11/1999 | Villas et al. ................ 604/110 |

* cited by examiner

*Primary Examiner*—Steven J. Ganey
(74) *Attorney, Agent, or Firm*—Burns, Doane, Swecker & Mathis LLP

(57) ABSTRACT

A catheter and system for delivering viscous fluid, under high pressures, into the vasculature of a patient includes a catheter body having a proximal end and a distal end, a reinforcing member surrounding at least a portion of the proximal end, and a compression fitting surrounding the reinforcing member for holding the proximal end of the catheter body. A strain relief element shrouds a portion of the proximal end to prevent kinking of the catheter body. Accordingly, the reinforcing member, the compression fitting and the strain relief element cooperate to hold the catheter body in a luer fitting and to prevent the proximal end of the catheter body from kinking under bending, and to prevent leakage or bursting under pressure.

22 Claims, 4 Drawing Sheets

HIGH PRESSURE INJECTION SYSTEM

FIELD OF THE INVENTION

This invention pertains to catheters for injecting viscous fluid into the body, and particularly to catheters that deliver viscous embolization agents into the vasculature.

BACKGROUND

Catheters have been used for decades to infuse fluids into the blood stream. For the most part, the infused fluids disperse in the blood to effectuate treatment of the patient.

The assignee of the present invention is a developer of bio-compatible agents that are particularly useful for embolization of diseased (e.g. aneurysmal) sites in the vasculature of a patient. U.S. Pat. No. 5,851,508, issued Dec. 22, 1998, describes various embolization agents. The disclosure of this U.S. patent is incorporated herein by reference. These embolization agents are typically insoluble in blood and are highly viscous to enable delivery to a particular situs in the vasculature without dispersion.

Delivery catheters used for dispensing embolization agents have been made sturdy enough to deliver the embolization agents to various parts of the vascular system. However, such catheters are often too large in diameter to effectuate treatment in the distal most reaches of the vasculature.

The diagnosis and treatment of neurovasculature disease can be of the utmost importance because neurovasculature disease (e.g. aneurysmal disease) could devastate the patient. Unfortunately, the vessels of the distal reaches of the neurovasculature are tortuous, having diameters of 3 mm, or less, and having bends exceeding 90 degrees. Tortuous vessels are difficult to reach with full-sized delivery catheters.

The amount of pressure required to dispense a viscous fluid from a small diameter tube is much greater than the pressure required to dispense the same fluid through a larger diameter tube. Accordingly, the smaller the delivery catheter, the higher the pressure required to deliver the viscous fluid.

Pressure experienced by a viscous fluid delivery catheter is normally greatest at the proximal end. The pressure decrease towards the distal end, approaching zero at the distal most tip. In testing, standard luer fittings (e.g. ISO 594-1 standard luer fittings) may fail when supplied with pressures exceeding 500 psi. Typically, a leak between the luer fitting and the catheter denotes a failure. Further, standard syringes may fail when used for pressing highly viscous fluid through catheters having relatively small diameters.

What is desired is a viscous fluid delivery system that can deliver viscous fluids to the distal reaches of the vasculature, including the neurovasculature. What is also desired is a micro-catheter that can withstand high pressures to deliver viscous fluids.

SUMMARY

A catheter for delivering viscous fluid into the vasculature of a patient includes a catheter body having a proximal end and a distal end, a reinforcing member surrounding at least a portion of the proximal end, and a compression fitting surrounding the reinforcing member for holding the proximal end of the catheter body.

The reinforcing member prevents radial compression and/or expansion of the proximal end of the catheter body, thus enabling the use of a compression fitting to hold the proximal end. The reinforcing member is tube-shaped and is either inserted within the proximal end, surrounds the proximal end, or both.

According to one aspect of the invention, the reinforcing member is integrated in the proximal end of the catheter body to resist radial deformation of the catheter body.

According to one aspect of the invention, the reinforcing member includes a tube that fully surrounds the proximal end. The tube is rigid, being fabricated from a tube of stainless steel less than 0.5" long that bonds to the proximal end.

Preferably, the compression fitting threads into a luer fitting and thus connects the luer fitting and the proximal end in fluid communication to enable viscous fluid to be delivered via the luer fitting and through the distal end of the catheter.

A sheath covers the reinforcing member. The sheath is compressible to enable the compression fitting to squeeze the sheath and thereby grip the reinforcing tube. Preferably, the sheath is fabricated of like material as the proximal end of the catheter body and is preferably over-molded around the stainless steel tube of the reinforcing member. Accordingly, the sheath integrates the reinforcing member in the catheter body.

The catheter includes a luer fitting with threaded connectors. The compression fitting threadibly attaches the proximal end of the catheter body to the luer fitting.

According to one aspect of the invention, the compression fitting includes a locknut having a threaded outer surface and an inner surface. The inner surface defines an opening for circumscribing the reinforcing member. The outer surface of the locknut has threads. When the locknut threads into a luer fitting, for example, the inner surface presses against the proximal end and the reinforcing member of the proximal end of the catheter body. The reinforcing member thus prevents significant deformation such as a significant reduction of the inner diameter of the proximal end by the locknut.

The luer fitting includes a strain relief element that covers the compression fitting and a portion of the proximal end to inhibit radial deformation of the proximal end when a viscous fluid is delivered by the catheter. Preferably, the strain relief element attaches to the compression fitting.

Many ways of attaching the strain relief element to the catheter are possible. According to one aspect of the invention, the strain relief element attaches directly to the luer fitting. In a further aspect, the strain relief element attaches to both the luer fitting and to the compression fitting. According to another aspect of the invention, the strain relief element bonds to the compression fitting. According to another aspect of the invention, the strain relief element and the compression fitting press-fit. According to yet another aspect of the invention, the compression fitting has an annular recess that holds the strain relief element. According to still another aspect of the invention, the strain relief element bonds to both the compression fitting and to the proximal end of the catheter body.

The strain relief element tapers from the luer fitting towards the catheter body to eliminate the possibility of kinking the catheter body during normal use. The taper may assume any of a variety of configurations. Preferably, however, the taper extends between 1"–3", and more preferably, the taper extends about 1.5".

A system in accordance with the present invention includes the catheter and a high pressure device for delivering viscous fluid to the catheter. The high pressure device includes a syringe having a blunt needle. The needle includes a removable barb press-fit on the blunt needle. The barb is configured for piercing a vial holding viscous fluid to enable the syringe to draw the viscous fluid from the vial. The barb slides off of the needle when the needle is removed from the vial.

A method of filling a syringe with viscous fluid in accordance with the present invention includes providing a syringe having a needle and a vial of viscous fluid, press fitting a removable barb on the blunt needle, piercing the vial with the barb, drawing viscous fluid into the syringe from the vial, and removing the needle from the vial and thereby causing barb to slide off of the needle so that the barb remains in the vial. Another step in accordance with this method includes inserting the needle into a catheter and delivering the viscous fluid to the neurovasculature of a patient via the catheter.

The dimensions of the catheter body are preferably adapted for accessing the distal and tortuous reaches of the neurovasculature. Accordingly, the distal end has an outside diameter of 0.040" or less to facilitate insertion of the catheter into tortuous regions of the vasculature. More preferably, the distal end has an outside diameter of less than 0.029".

The distal end further includes a delivery lumen with lumen walls. The lumen walls being at least 0.0012" thick to withstand pressures associated with the delivery of a viscous fluid. The proximal end of the catheter body being configured for attachment to a luer fitting and for withstanding pressures exceeding 2000 psi. Also, the syringe, the luer fitting and medial portions of the catheter body are also configured for withstanding pressures of 2000 psi or more.

The syringe attaches to the luer fitting with a syringe locknut. The syringe needle inserts into the syringe locknut and the syringe locknut to holds the needle when the syringe locknut threads into the luer fitting.

According to one aspect of the luer fitting, the luer fitting is bifurcated, having a three threaded portions to simultaneously receive and attach two syringes to two of the threaded portions, and to attach the compression fitting and the catheter body to the remaining threaded portion, respectively.

DETAILED DESCRIPTION

Figure 1:
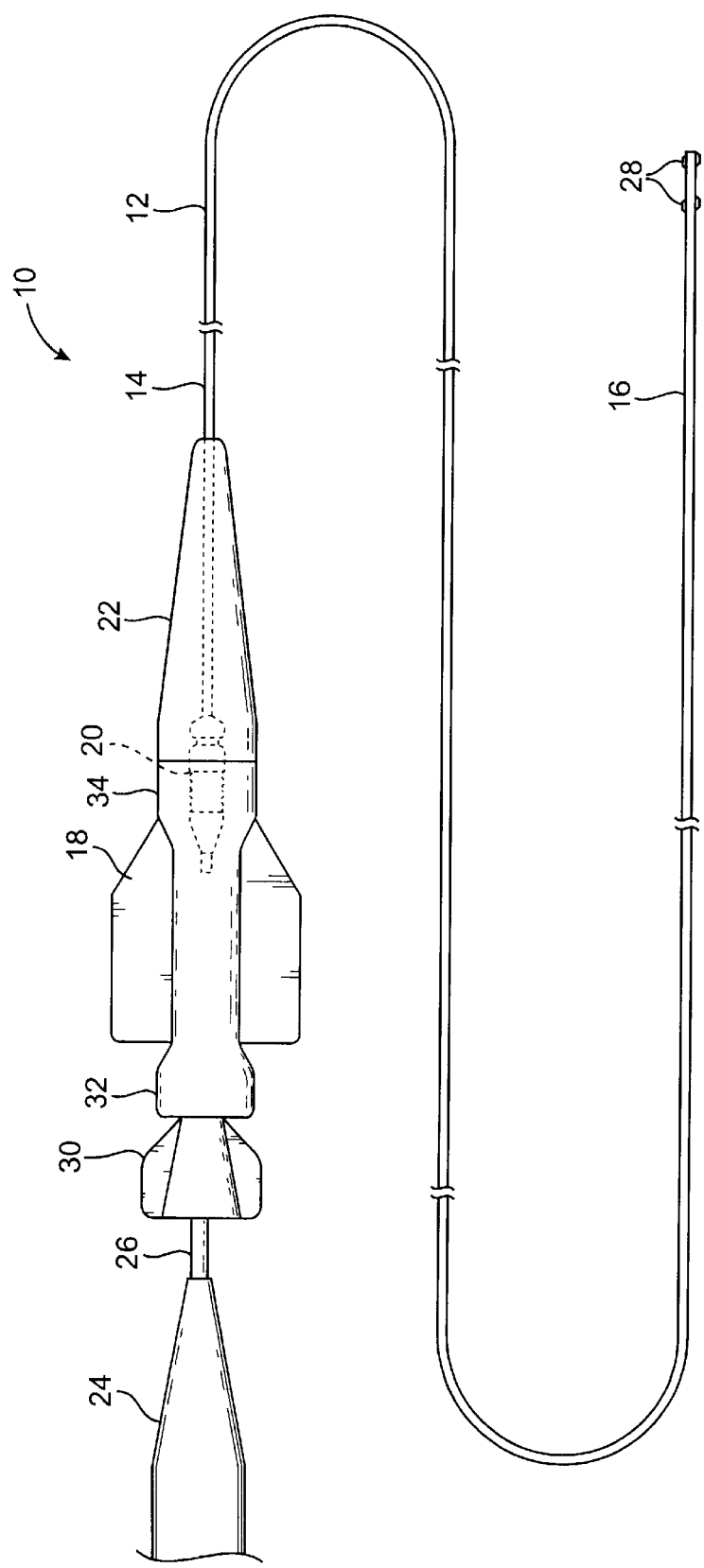
FIG. 1 is a side view of a catheter in accordance with the present invention.

FIG. 1 shows a catheter generally designated with the reference numeral 10. The catheter 10 includes a catheter body 12 with a proximal end 14 and a distal end 16. The catheter 10 also includes a luer fitting 18 with a compression fitting 20 and a strain relief element 22. The compression fitting 20 attaches the proximal end 14 of the catheter body to the luer fitting 18.

The catheter 10 has a syringe 24 with a needle 26 inserted into the luer fitting 18. The syringe 24 includes a syringe locknut 30 that removably attaches the luer fitting 18 to the syringe 24 in fluid communication. The syringe 24 is capable of delivering viscous fluid under pressures of at least between 1000 psi and 2000 psi.

The catheter 10 is particularly designed for delivering viscous fluids at high pressures to within the body of a patient. While the catheter 10 can be used within the digestive track, and in various internal tissues and organs, the primary use for the catheter 10 is to deliver embolization agents to address aneurysmal disease. Accordingly, the catheter 10 is sized for use in tortuous regions of the vasculature in order to reach the distal reaches of the neural vasculature, where aneurysmal disease can have great impact.

Commonly assigned U.S. Pat. Nos. 5,667,767, 5,580,568, 5,830,178, and 6,051,607 describe various embolization agents including cellulose diacetate compositions, dimethylsulfoxide compositions, and Ethyl Lactate compositions, having relatively high viscosity, that are injectable in a viscous fluid form into a diseased or injured portion of the vasculature to improve the blood vessel integrity. The disclosures of these U.S. patents are incorporated herein by reference.

Some of these embolization agents, and others, have been successfully used to fill aneurysms, thereby structurally strengthening the blood vessel. Methods of embolizing blood vessels are described in commonly assigned U.S. Pat. Nos. 5,702,361 and 6,017,977, the disclosures of which are incorporated herein by reference.

During a vascular application, the viscous embolization agent typically injects via a vascular catheter without dispersion in the blood. The viscous embolization agent sets over a period to structurally strengthen the blood vessel.

While it can be appreciated that embolization agents are used in the vasculature, there are many other applications for such embolization agents such as to treat urinary incontinence, to facilitate plastic surgery, to treat ruptured spinal disks, gynecologic dysfunction, treating endoleaks, etc. The present invention can be applied to these applications, and more. Further, while the catheter 10 disclosed herein is used to inject the agents is typically a vascular catheter, the geometry and integrity of the catheter 10 can be particularly adapted to address virtually any site within the body. The catheter 10 is useful for dispersing both dispersable and non-dispersable embolization agents.

The luer fitting 18 has two ends 32 and 34. Both of the ends 32 and 34 have internal threads. The end 34 is threaded for receiving the compression fitting 20. The end 32 receives either an introducer locknut that is sized in accordance with ISO 594-1, or a syringe locknut 30. An introducer locknut of standard configuration is used prior to attachment of the high pressure syringe for introduction of a guidewire, contrast agent, saline, medicine or any other adapter requiring an ISO 594-1 standard luer fitting connection.

The syringe locknut 30 that holds the needle 26 of the syringe 24 in the end 32. Removal of the syringe locknut 30, and the syringe 24, enables alternate attachment of a second syringe to the end 32 of the luer fitting 18.

The proximal end 14 of the catheter body 12 attaches to the end 34 of the luer fitting to enable the luer fitting 18 and the proximal end 14 of the catheter body 12 to withstand operational pressure exceeding 2000 psi. The compression fitting 20 attaches the proximal end 14 of the catheter body to the luer fitting 18. The compression fitting 20 enables the luer fitting 18 and the proximal end 14 of the catheter body 12 to withstand high operational pressures.

The distal end 16 of the catheter body 12 includes marker bands 28 to enable an operator to locate the distal end 16 during use. The distal end 16 is particularly configured for accessing tortuous regions of the neurovasculature. Tortuous regions are defined as those vascular regions having bend exceeding 90 degrees and having a vascular diameter of 3 mm or less. Accordingly the distal end 16 has an outside diameter of 0.040" or less. The distal end includes a delivery lumen with lumen walls, the lumen walls being at least 0.0012" thick to withstand pressures associated with the delivery of viscous fluids.

Figure 2:
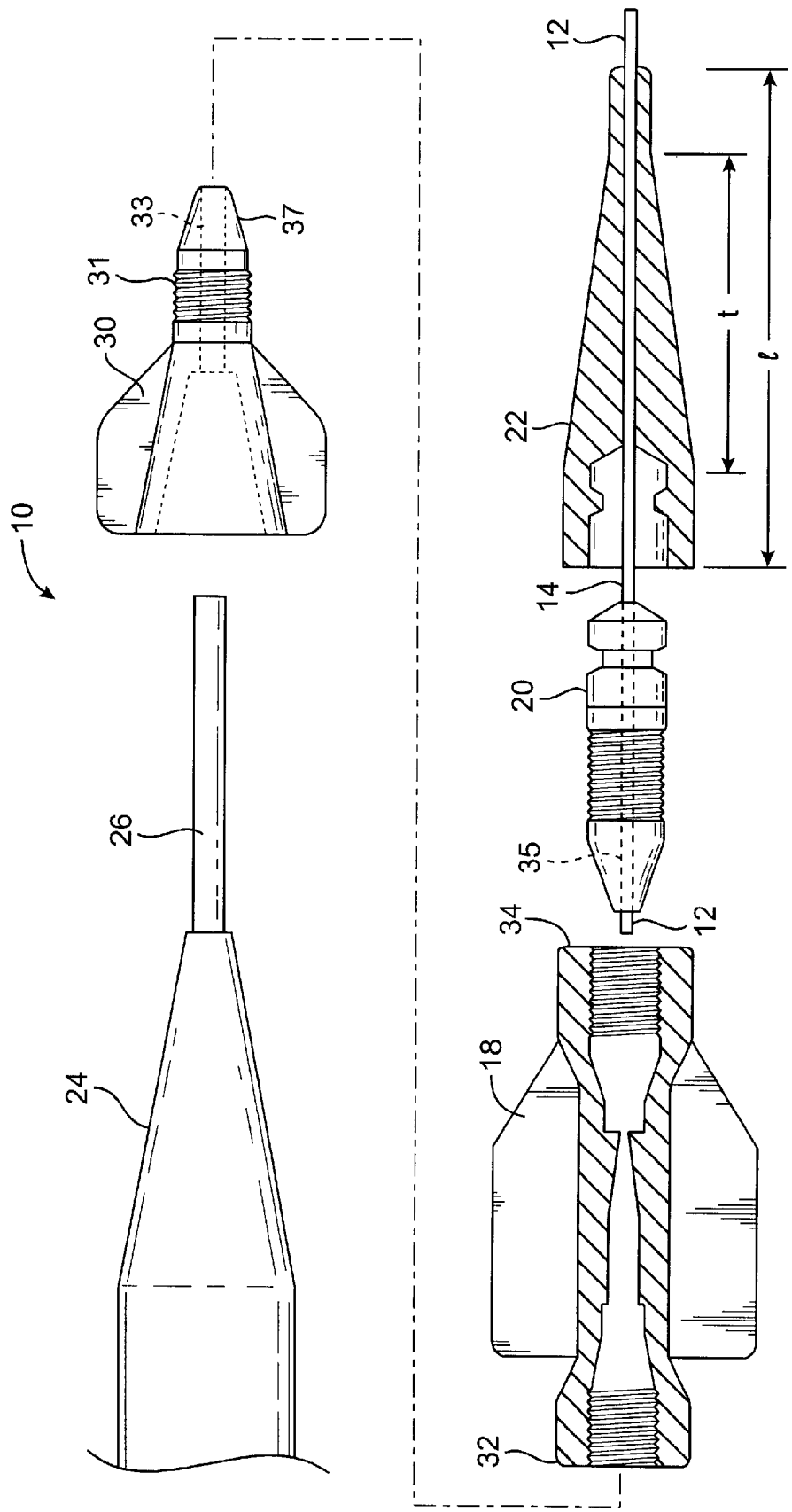
FIG. 2 is an exploded view of the catheter of FIG. 1 shown partly in cross-section.

FIG. 2 shows the syringe 24, the syringe locknut 30, the luer fitting 18, the compression fitting 20, the catheter body 12 and the strain relief element 22. The syringe locknut 30 is one form of compression fitting. There are other compression fittings, however, including compression fittings formed from thermal bonding techniques, insert-moldings and over-moldings, for examples. These alternate forms of compression fittings can be substituted for the syringe locknut 30 in accordance with the present invention.

The syringe locknut 30 is hollow, having a centrally defined opening 33 for receiving the needle 26 of the syringe 24. The syringe locknut 30 compresses against the needle 26 to hold and seal the needle 26.

The syringe locknut 30 includes a threaded portion 31 and an angled section 37. The syringe locknut 30 rotates to thread the threaded portion 31 to the end 32 of the luer fitting 18. When the needle 26 inserts into the luer fitting 18, and the syringe locknut 30 slide forward in place with respect to the luer fitting 18 and rotates, the needle 26 does not significantly deform, instead, the angled section 37 of the syringe locknut 30 radially compresses to hold the needle 26 within the opening 33.

The compression fitting 20, according to one aspect of the invention, is a locknut that radially compresses to hold the proximal end 14 of the catheter body 12 when threaded to the luer fitting 18. The compression fitting 20 includes an opening 35 axially defined in the compression fitting 20. When the proximal end 14 of the catheter body 12 inserts into the opening 35, and the compression fitting 20 rotates to thread into the end 34 of the luer fitting 18, then the compression fitting radially compresses against the proximal end 14 of the catheter body 12.

In order to allow the compression fitting to hold the proximal end 14 of the catheter body, the proximal end 14 has a rigid tip 39 that resists radial compression.

The compression fitting 20 includes an annular recess that holds the strain relief element 22. The strain relief element 22 thus attaches to the luer fitting 18. It can be appreciated, however, that there are many ways to attach the strain relief element 22 to the luer fitting 18.

The strain relief element 22 includes a length "l". A portion of the length "l" has a taper "t". The taper "t" extends in a direction from the luer fitting towards the catheter body 12 to support the proximal end 14 of the catheter body 12. Preferably, the taper extends between 1"–3", and more preferably the taper extends about 1.5".

The strain relief element 22 is soft to support proximal end 14 and to allow flexibility of the proximal end 14, while minimizing any potential for kinking of the proximal end 14.

Figure 3:
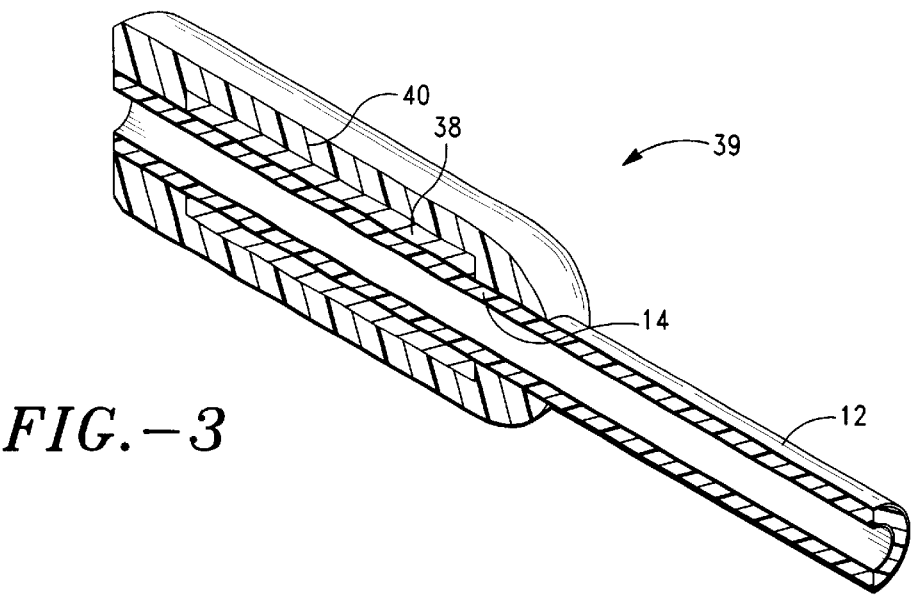
FIG. 3 is a cross-section of the proximal end of a catheter body in accordance with the present invention.

FIG. 3 shows the rigid tip 39 of the catheter body 12. The rigid tip 39 includes a portion of the proximal end 14, a reinforcing member 38 and a sheath 40. The reinforcing member 38 surrounds at least a portion of the proximal end 14 to inhibit radial deformation. The sheath 40 surrounds the reinforcing member 38.

According to an alternate aspect of the invention, the reinforcing member 38 is sized to insert into the proximal end 14 to inhibit radial deformation. According to a further aspect of the invention, the reinforcing member is undermolded in place with respect to the proximal end 14.

The reinforcing member 38 is preferably a band of stainless steel that circumscribes the proximal end 14 to enable the proximal end 14 to resist deformation caused by the compression fitting 20 (FIG. 2). The reinforcing member 38 also prevents radial expansion of the proximal end 14. Preferably the reinforcing member 38 has a length that does not exceed a length of the compression fitting 20. However, it can be appreciated that the length can be modified if operating pressures require the proximal end 14 to have additional reinforcement.

Figure 4:
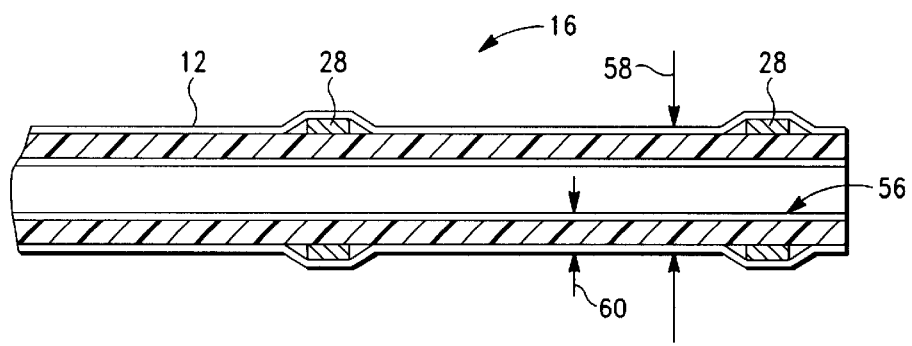
FIG. 4 is a cross-section of the distal end of a catheter body in accordance with the present invention.

FIG. 4 shows the marker bands 28 circumscribing the distal end 16 of the catheter body 12. The catheter body 12 is hollow, defining a viscous fluid delivery lumen 56. The catheter body has an outside diameter 58 of 0.040" or less to facilitate insertion of the distal end 16 into tortuous regions of the vasculature. The distal end 16 includes lumen walls 60. The lumen walls 60 are at least 0.0012" thick to withstand pressures associated with delivery of viscous fluid. Preferably, the delivery lumen 56 has an inside diameter of 0.025" or less. For some applications, the delivery lumen 56 is adapted to have an inside diameter of less than 0.005".

Figure 5:
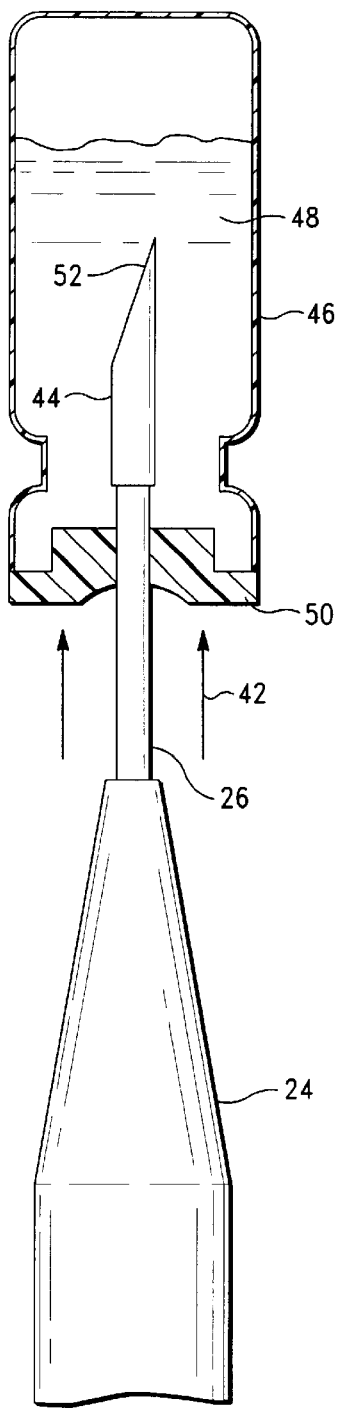
FIG. 5 is a shows a syringe inserted into a vial of viscous fluid.

FIG. 5 shows the syringe 24 having a barb 44 with a sharpened tip 52 attached to the needle 26 in a friction fit around the needle 26. The syringe 24 inserts into a vial 46 of viscous fluid 48 in the direction of the arrow 42.

The syringe 24 includes a blunt needle 26. The barb 44 is removable and press-fits on to the needle 26. The vial 46 has a cap 50.

A method of filling the syringe 24 with viscous fluid 48 includes press-fitting the removable barb 44 on the blunt needle 26. The next step includes piercing the cap 50 of the vial 46 with the tip 52 of the barb 44. Further inserting the barb 44 and the needle 26 enables access to the viscous fluid 48. The syringe draws the viscous fluid 48 via the needle 26 from the vial 46 and into the syringe 24. Although a syringe 24 is used to withdraw the viscous fluid 48, it can be appreciated that other mechanisms can withdraw fluid from a vial.

Figure 6:
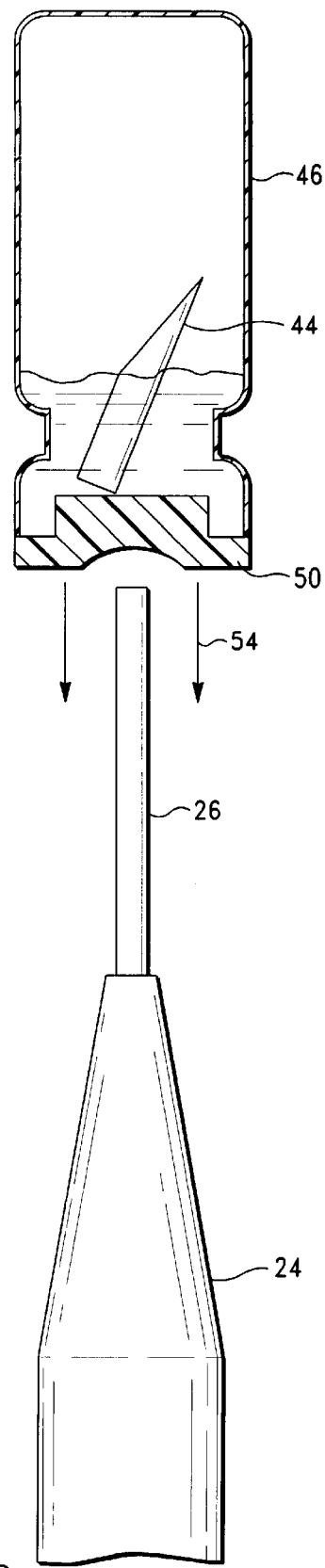
FIG. 6 shows the syringe of FIG. 5 withdrawn from the vial.

FIG. 6 shows the syringe 24 and needle 26 removing from the vial 46. The cap 50 remains fixed on the vial 46. Withdrawal of the syringe in the direction of the arrow 54 causes the barb 44 to slide off the needle 26. The barb 44 remains in the vial 46. Accordingly, movement of the syringe 24 and the integrity of the cap cooperate to cause the barb 44 to slide off of the needle 26.

Once the syringe 24 is filled with viscous fluid 48, the needle 26 is inserted into the luer fitting 18 (FIG. 1) for delivering the viscous fluid to a patient via the catheter.

Figure 7:
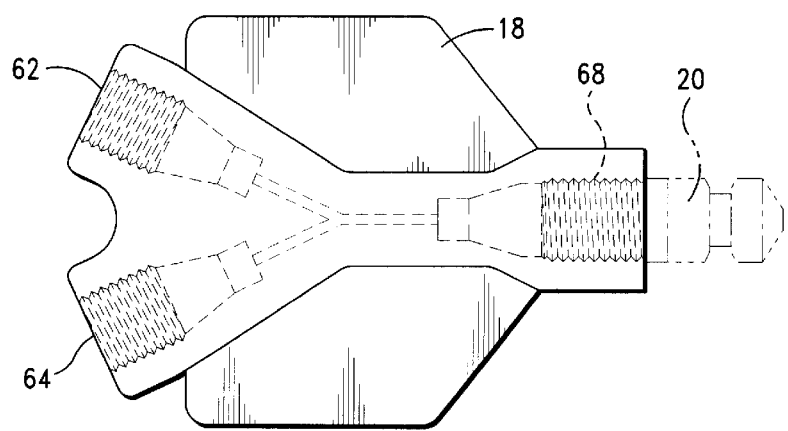
FIG. 7 shows an alternate embodiment of a luer fitting in accordance with the present invention.

FIG. 7 shows an embodiment of the luer 18 having a bifurcated design. The luer fitting 18 has three of threaded portions 62, 64 and 68. The threaded portion 68 attaches to the compression fitting 20. The threaded portions 62 and 64 attach, respectively to fluid delivery systems such as syringes.

While the present invention is described in terms of particular embodiments shown in the drawings, there are various ways to design, assemble and use the invention which may depart from the exemplary description provided herein. Accordingly, the claims should be limited only by the claims as set forth below.

What is claimed is:

1. A catheter for delivering viscous fluid into the vasculature of a patient, comprising:
   a catheter body having a proximal end and a distal end;
   a reinforcing member surrounding at least a portion of the proximal end of the catheter body; and
   a compression fitting surrounding the reinforcing member for holding the proximal end of the catheter body.

2. A catheter as set forth in claim 1, wherein the reinforcing member includes a tube that fully surrounds the proximal end.

3. A catheter as set forth in claim 1, wherein the reinforcing member is rigid, being fabricated from a tube of stainless steel less than 0.5" long, and being bonded to the proximal end.

4. A catheter as set forth in claim 1, further comprising a sheath covering the reinforcing member, the sheath is compressible to enable the compression fitting to squeeze the sheath and thereby grip the reinforcing tube.

5. A catheter as set forth in claim 4, wherein the sheath is over-molded around the reinforcing member.

6. A catheter as set forth in claim 1, wherein the compression fitting includes a locknut having an outer surface and an inner surface, the inner surface defining an opening for circumscribing the reinforcing member, the outer surface having threads for engaging a luer fitting, whereby when the locknut engages a luer fitting, the inner surface presses against the proximal end and the reinforcing member of the catheter body prevents significant deformation of the proximal end.

7. A catheter as set forth in claim 1, further comprising a luer fitting, the compression fitting attaches the proximal end to the luer fitting, the luer fitting including a strain relief element that covers the compression fitting and a portion of the proximal end to inhibit kinking of the proximal end.

8. A catheter as set forth in claim 7, wherein the strain relief element tapers from the luer fitting towards the catheter body to reinforce the proximal end of the catheter body.

9. A catheter as set forth in claim 8, wherein taper extends between 1"–3".

10. A catheter as set forth in claim 9, wherein taper extends about 1.5".

11. A catheter for delivering viscous fluid into the vasculature of a patient, comprising:
    a catheter body having a proximal end and a distal end, the proximal end of the catheter body being capable of withstanding pressures of over 2000 psi to facilitate delivery of a viscous fluid;
    a luer fitting;
    a compression fitting surrounding the proximal end of the catheter body;
    a strain relief element extending over a portion of the proximal end of the catheter body to inhibit kinking of the proximal end of the catheter body; and a reinforcing means attached to the proximal end to resist radial deformation of the proximal end.

12. A catheter for delivering viscous fluid into the vasculature of a patient, comprising:
    a catheter body having a proximal end and a distal end, the proximal end or the catheter body being capable of withstanding pressures of over 2000 psi to facilitate delivery of a viscous fluid;
    a luer fitting;
    a compression fitting surrounding the proximal end of the catheter body;
    a strain relief element extending over a portion or the proximal end of the catheter body to inhibit kinking of the proximal end of die catheter body; wherein the strain relief element bonds to the compression fitting.

13. A catheter for delivering viscous fluid into the vasculature of a patient, comprising:
    a catheter body having a proximal end and a distal end, the proximal end of the catheter body being capable of withstanding pressures of over 2000 psi to facilitate delivery of a viscous fluid;
    a luer fitting;
    a compression fitting surrounding the proximal end of the catheter body;
    a strain relief element extending over a portion of the proximal end of the catheter body to inhibit kinking of the proximal end of the catheter body; wherein the compression fitting has an annular recess that holds the strain relief element.

14. A catheter for delivering viscous fluid into the vasculature of a patient, comprising:
    a catheter body having a proximal end and a distal end, the proximal end of the catheter body being capable of withstanding pressures of over 2000 psi to facilitate delivery of a viscous fluid;
    a luer fitting;
    a compression fitting surrounding the proximal end of the catheter body;
    a strain relief element extending over a portion of the proximal end of the catheter body to inhibit kinking of the proximal end of the catheter body, wherein the strain relief element bonds to the compression fitting and to the proximal end of the catheter body.

15. A fluid injection system for delivering viscous fluid into the vasculature of a patient, comprising:
    a catheter body having a proximal end and a distal end, the distal end having an outside diameter of 0.040" or less to facilitate insertion of the catheter into tortuous regions of the vasculature, the distal end includes a delivery lumen with lumen walls, the lumen walls being at least 0.0012" thick to withstand pressures associated with the delivery of a viscous fluid;
    the proximal end being configured for attachment to a luer fitting and for withstanding pressures exceeding 2000 psi, a catheter locknut and luer, the luer having a first threaded portion and a second threaded portion, the locknut has an inner surface defining an opening that surrounds the proximal end of the catheter body, the locknut attaches to the first threaded portion of the luer fitting to attach the proximal end of the catheter body to the luer fitting.

16. A fluid injection system as set forth in claim 15, further comprising:
    a syringe capable of delivering viscous fluid at pressures of over 1000 psi to the luer; and
    a means for attaching the syringe to the luer.

17. A fluid injection system as set forth in claim 16, wherein the syringe includes a needle, the means for attaching the syringe to the luer fitting includes a syringe locknut, the needle inserts into the locknut and the locknut threads to the syringe to hold the needle within the second threaded portion of the luer fitting.

18. A fluid injection system as set forth in claim 17, wherein the luer is bifurcated, having a third threaded portion to simultaneously attach two syringes to the second and third threaded portions, respectively.

19. A syringe for use with viscous fluids, comprising:

a syringe having a blunt needle; and a removable barb press fit on the blunt needle for piercing a vial holding viscous fluid to enable the syringe to draw the viscous fluid from the vial;

whereby, the barb slides off of the needle when the needle is removed from the vial.

20. A syringe as set forth in claim 19 wherein the syringe includes a locknut, the locknut surrounds the needle in a friction fit.

21. A method of filling a syringe with viscous fluid, comprising:

providing a syringe having a blunt needle and a vial of viscous fluid;

press fitting a removable barb on the blunt needle;

piercing the vial with the barb;

drawing viscous fluid into the syringe from the vial; and removing the needle from the vial and hereby causing barb to slide off of the needle so that the barb remains in the vial.

22. A method of delivering a viscous fluid to a patient via the catheter, comprising:

filling a syringe with viscous fluid, by:

(a) providing a syringe having a blunt needle and a vial of viscous fluid;

(b) press fitting a removable barb on the blunt needle;

(c) piercing the vial with the barb;

(d) drawing viscous fluid into the syringe from the vial; and (e) removing the needle from the vial and thereby causing barb to slide off of the needle so that the barb remains in the vial; and then inserting the needle into the catheter and delivering the viscous fluid to a patient via the catheter.

* * * * *